United States Patent [19]

Fedorov et al.

[11] Patent Number: 4,884,569

[45] Date of Patent: Dec. 5, 1989

[54] DEVICE FOR OPHTHALMOLOGIC OPERATIONS

[75] Inventors: Svyatoslav N. Fedorov; Sergei A. Soloviev; Evgeny I. Degtev; Albina I. Ivashina; Alexandr A. Karavaev, all of Moscow, U.S.S.R.

[73] Assignee: Mezhotraslevoi Nauchno-tekhnichesky Komplex "Mikrokhirurgia Glaza", Moscow, U.S.S.R.

[21] Appl. No.: 162,334

[22] PCT Filed: Mar. 31, 1986

[86] PCT No.: PCT/SU86/00028

§ 371 Date: Nov. 23, 1987

§ 102(e) Date: Nov. 23, 1987

[87] PCT Pub. No.: WO87/05799

PCT Pub. Date: Oct. 8, 1987

[30] Foreign Application Priority Data

Jul. 5, 1983 [SU] U.S.S.R. .................... 3615522

[51] Int. Cl.⁴ .................... A61B 17/32
[52] U.S. Cl. .................... 128/305

[58] Field of Search .............. 128/305; 30/320, 329, 30/337

[56] References Cited

U.S. PATENT DOCUMENTS 3,967,377 7/1976 Wells .................... 30/320
4,473,076 9/1984 Williams et al. .................... 128/305
4,499,898 2/1985 Knepshield et al. .................... 128/305

FOREIGN PATENT DOCUMENTS 3300567 8/1983 Fed. Rep. of Germany .
959779 9/1982 U.S.S.R. .
1016882 12/1984 U.S.S.R. .

*Primary Examiner*—Michael H. Thaler
*Attorney, Agent, or Firm*—Fleit, Jacobson, Cohn, Price, Holman & Stern

[57] ABSTRACT

A device for ophthalmologic operations comprised of a holder (1), a cutting instrument (9) provided with a catch (10) and secured on a spring-loaded rod (7) accommodated inside of the holder (1) and having a micrometric thread (11) on the other end. Mounted on the holder (1) by means of a micrometric thread (15) is a thrust bushing (14) which carries the catch which fixes the position of this bushing (14) and is interconnected with a nut by which the rod (2) is moved.

4 Claims, 1 Drawing Sheet

4,884,569

DEVICE FOR OPHTHALMOLOGIC OPERATIONS

TECHNICAL FIELD

The present invention relates to surgical instruments and, more specifically, to devices for ophthalmologic operations.

BACKGROUND OF THE INVENTION

Known in the prior art is a device for ophthalmologic operations comprising a holder carrying a longitudinally-movable cutting instrument and a stop (cf., SU, A, 1016882).

This device fails to provide for a sufficiently high standard of surgical operations since the incision does not follow the required ideal curve.

Another device for ophthalmologic operations known in the prior art comprises a holder and a stop located on said holder and interacting with the surface of the eye cornea during the operation. The holder accommodates a spring-loaded rod one end of which carries a cutting instrument with a catch while its other end is provided with a micrometric thread for moving said rod inside the holder by means of a nut.

Such device also fails to provide a sufficiently high accuracy of setting the cutting instrument to the present value which impairs the accuracy of the operation.

Besides, the device is difficult to handle which affects adversely the quality of surgery and requires a certain time to get the device ready for use, thus impairing its efficiency.

SUMMARY OF THE INVENTION

The main object of the invention is to provide a device for ophthalmologic operations which would ensure a high accuracy of setting the cutting instrument to the desired value by modifying the design of instrument-setting elements.

This object is accomplished by providing a device for ophthalmologic operations comprising a holder, a stop located on said holder and interacting with the surface of eye cornea during the operation, a cutting instrument with a catch secured on a spring-loaded rod accommodated inside the holder and carrying a micrometric thread on the other end, said thread intended for moving said rod inside of said holder, and a nut interacting with said rod for moving the latter which, according to the invention, has a thrust bushing mounted on the holder by means of the micrometric thread cut at the side opposite to the stop, and a catch which fixes the position of the thrust bushing relative to the holder, said catch being installed on the thrust bushing and interconnected with the nut.

This design promotes the accuracy of setting the stop and, consequently, the cutting instrument with relation to the eye cornea.

It is expedient that the catch of the thrust bushing should contain a spring-loaded lever whose axle is hinged on the external side surface of said bushing and whose one end interacts with the slots on the holder and thrust bushing, said slots getting in line for fixing the position of the thrust bushing, the slot on the thrust bushing being of a through type, and the other end of the lever interacts with the nut by means of flutes made on both of them.

It is likewise expedient that the micrometric thread of the rod and thrust bushing should have different pitches.

BRIEF DESCRIPTION OF THE DRAWINGS

Now the invention will be described in detail by way of example with reference to the appended drawings in which.

BEST MODE FOR CARRYING OUT THE INVENTION

Figure 1:
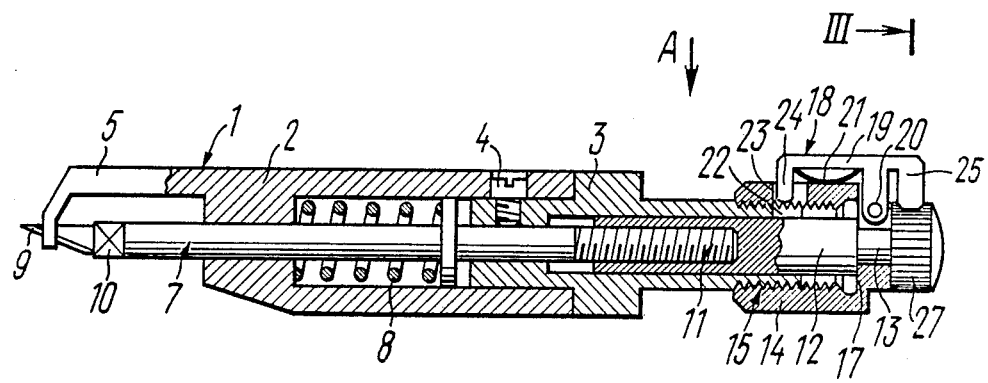
FIG. 1 shows a device for ophthalmologic operations according to the invention, longitudinal section.
Figure 2:
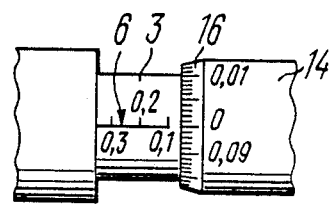
FIG. 2 shows the same device, view of micrometric screw scales along arrow A.

A device for ophthalmologic operations contains hollow holder 1 (FIG. 1) made up of two members 2 and 3 interconnected by screw 4. The member 2 of the holder 1 has a stop 5 interacting with the surface of eye cornea during operations while the member 3 of the holder 1 bears a coarse scale 6 (FIG. 2). Accommodated inside of the holder 1 (FIG. 1) is a rod 7 loaded by a spring 8, said rod carrying a cutting instrument 9 secured by a catch 10. The other end of the rod 7 has a micrometric thread 11 with a pitch $t_1$, said thread enabling the rod to interact via a shaft 12 with a nut 13 during installation of the cutting instrument 9.

The member 3 of the holder 1 carries a thrust bushing 14, also on a micrometric thread 15 of $t_2$ pitch, $t_1 \neq t_2$. The thrust bushing 14 bears a fine scale 16 (FIG. 2). The end of the shaft 12 is pressed against an internal surface 17 (FIG. 1) of the bushing 14. The bushing 14 mounts a catch 18 for fixing its position relative to the holder 1.

The catch 18 comprises a lever 19 hinged on an axle 20 relative to the external side surface of the bushing 14, and loaded by a spring 21.

Figure 3:
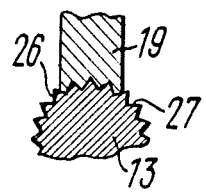
FIG. 3 shows the same device, section along line III—III in FIG. 1.

The member 3 of the holder 1 has a slot 22 while the thrust bushing 14 has a through slot 23, both slots interacting with an arm 24 of the lever 19. The other arm 25 of the lever 19 has flutes 26 (FIG. 3) matching with flutes 27 of the nut 13.

The device functions as follows.

The cutting instrument 9 is inserted into its catch 10. Then the lever 19 of the catch 18 is pressed by a finger to align the slot 23 of the thrust bushing 14 with the slot 22 of the holder 1. The arm 24 of the lever 19 snaps into slots 22 and 23.

At this position of the thrust bushing 14 with relation to the holder 1 the zero positions of the coarse scale 6 and the fine scale 16 coincide and are fixed. The nut 13 does not interact with the thrust bushing 14 since flutes 26 do not engage flutes 27 of the nut 13. Then, by rotating the nut 13 the cutting instrument 9 is set flush with the surface of the stop 5. Now, the lever 19 is pressed by a finger and the spring 21 forces said lever away from the side surface of the thrust bushing 14 while the arm 24 comes out of slots 23 and 22 of the thrust bushing 14 and the holder 1, respectively. Due to a hinged installation of the lever 19 on the thrust bushing 14, flutes 26 of said lever engage flutes 27 of nut 13.

Then, by rotating the nut 13 (or the thrust bushing 14), the cutting instrument 9 is set by scales 6 and 16 of the holder 1 and the thrust bushing 14 to the preset value corresponding to the required depth of incision and the instrument is in full readiness for use.

Inasmuch as the nut 13 interacts with the thrust bushing 14 and the end of the shaft 12 is pressed against the internal face surface 17 of the thrust bushing 14, one revolution of the nut 13 moves out the cutting instrument 9 through a distance equal to the difference in the thread pitches of the nut 13 and the thrust bushing 14.

The utilization of the claimed device steps up the accuracy of the surgical operation 10 times approximately.

This gain in accuracy is secured because the design of the claimed device ensures a small feed of the cutting instrument per revolution of the nut and an accurate setting of the device in the zero position thus making it possible, if necessary, to replace an instrument blunted in the course of the operation.

INDUSTRIAL APPLICABILITY

The device is applicable for making nonpenetrating cornea incisions of a preset depth and shape during operations on the eye with a view to changing ocular refraction.

We claim:

1. A device for ophthalmologic operations comprising a holder (1), a stop (5) arranged on said holder at one end of the holder for interacting with a surface of an eye cornea during an operation, a cutting instrument (9) with a catch (10) secured on one end of a spring-loaded rod (7) which is accommodated inside the holder (1) and carries a micrometric thread (11) on its other end for moving said rod inside the holder (1), a nut (13) interacting with the rod (7) for moving the latter by rotation of the nut, a thrust bushing (14) threaded on the holder (1) by means of a further micrometric thread (15) at an end of the holder opposite to the stop (5), and a further catch (18) releasably fixing the position of the thrust bushing (14) relative to the holder (1), said further catch (18) being mounted on the thrust bushing (14) and being releasably engageable with the nut (13) so as to allow rotation of the nut when disengaged therefrom and prevent rotation of the nut when engaged therewith.

2. The device according to claim 1 characterized in that the further catch (18) comprises a spring-loaded lever (19) having an axle (20) hinged on the thrust bushing (14) and one arm (24) which interacts with respective slots (22, 23) on the holder (1) and on the thrust bushing (14), said slots (22, 23) engineered so as to be lined up for fixing the position of the thrust bushing (14), the slot (23) on said thrust bushing (14) being of a through type.

3. The device according to claim 2 characterized in that the lever has another arm (25) for releasable engagement with the nut (13) by means of flutes (26, 27) provided on both said another arm and the nut.

4. The device according to claim 1 characterized in that the micrometric threads (11) on the rod (7) and the micrometric threads (15) on the thrust bushing (14) have different pitches.

* * * * *